United States Patent [19]

Kelly et al.

[11] Patent Number: 5,371,205
[45] Date of Patent: Dec. 6, 1994

[54] PDGF α RECEPTOR

[75] Inventors: James D. Kelly; Mark J. Murray, both of Seattle, Wash.

[73] Assignee: ZymoGenetics, Inc., Seattle, Wash.

[21] Appl. No.: 947,358

[22] Filed: Sep. 18, 1992

Related U.S. Application Data

[63] Continuation of Ser. No. 355,018, May 22, 1989, abandoned.

[51] Int. Cl.$^5$ .................. C07H 21/02; C12Q 1/68; A61K 35/14; C12N 15/00
[52] U.S. Cl. ......................... 536/23.5; 435/6; 435/240.2; 435/255.1; 530/380; 935/13; 935/28; 935/37
[58] Field of Search ............ 435/6, 240.2, 255.1; 536/23.5; 935/13, 28, 37; 530/380

[56] References Cited

PUBLICATIONS

Yarden et al, Nature, v. 323, 1986, pp. 226–232.
Beggs, Nature, v. 275, 1978, 104–108.
Matsui et al, Science, vol. 243, (1989), pp. 800–804.
Mariatis et al, Molecular Cloning: X Laboratory Manual, Cold Spring Harbor Laboratory (1982) pp. 249–251.
Hart et al, J. Biol. Chem., vol. 262 (1987) pp. 10780–10785.
Heldin et al., "Binding of different dimeric forms of PDGF to human fibroblasts: evidence for two separate receptor types", *EMBO J.* 7:1387–1393, 1988.
Escobedo et al., "A Common PDGF Receptor Is Activated by Homodimeric A and B Forms of PDGF", *Science* 240:1532–1534, 1988.
Claesson–Welsh et al., *J. Biol. Chem.* 264:1742–1747, 1989.
Claesson–Welsh et al., *Proc. Natl. Acad. Sci. USA* 86:4917–4921, 1989.
Hart et al., *Growth Factors and Their Receptors: Genetic Control and Rational Application*, Alan R. Liss, Inc., 1989, pp. 297–305.
Gronwald et al., *Proc. Natl. Acad. Sci. USA* 85:3435–3439, 1988.
Hart et al., *Science* 240:1529–1531, 1988.
Daniel et al., *Proc Natl. Acad. Sci. USA* 82:2684–2687, 1985.
Claesson–Welsh et al., *Mol. Cell. Biol.* 8:3476–3486, 1988.

*Primary Examiner*—Mindy B. Fleisher
*Attorney, Agent, or Firm*—Seed and Berry

[57] ABSTRACT

Isolated DNA molecules that encode a novel PDGF receptor are disclosed. The receptor binds the AA, AB and BB isoforms of PDGF with high affinity. Cells transfected or transformed with the DNA molecules are also disclosed. The cells can be used within methods for detecting PDGF agonist or antagonist activity in a test compound.

10 Claims, 6 Drawing Sheets

Fig. 1A

```
  1 GCCCTGGGGACGGACCGTGGGCGGCGCGCAGCGGCGGGACGCGTTTTGGGGACGTGGTGGCCAGCGCCT
 70 TCCTGCAGACCCACAGGGAAGTACTCCCTTTGACCTCCGGGGAGCTGCGACCAGGTTATACGTTGCTGG
139 TGGAAAAGTGACAATTCTAGGAAAAGAGCTAAAAGCCGGATCGGTGACCGAAAGTTTCCCAGAGCTATG
                                                                       M
                                                                       1

208 GGGACTTCCCATCCGGCGTTCCTGGTCTTAGGCTGTCTTCTCACAGGGCTGAGCCTAATCCTCTGCCAG
     G  T  S  H  P  A  F  L  V  L  G  C  L  L  T  G  L  S  L  I  L  C  Q

277 CTTTCATTACCCTCTATCCTTCCAAATGAAAATGAAAAGGTTGTGCAGCTGAATTCATCCTTTTCTCTG
     L  S  L  P  S  I  L  P  N  E  N  E  K  V  V  Q  L  N  S  S  F  S  L

346 AGATGCTTTGGGGAGAGTGAAGTGAGCTGGCAGTACCCCATGTCTGAAGAAGAGAGCTCCGATGTGGAA
     R  C  F  G  E  S  E  V  S  W  Q  Y  P  M  S  E  E  E  S  S  D  V  E

415 ATCAGAAATGAAGAAAACAACAGCGGCCTTTTTGTGACGGTCTTGGAAGTGAGCAGTGCCTCGGCGGCC
     I  R  N  E  E  N  N  S  G  L  F  V  T  V  L  E  V  S  S  A  S  A  A

484 CACACAGGGTTGTACACTTGCTATTACAACCACACTCAGACAGAAGAGAATGAGCTTGAAGGCAGGCAC
     H  T  G  L  Y  T  C  Y  Y  N  H  T  Q  T  E  E  N  E  L  E  G  R  H

553 ATTTACATCTATGTGCCAGACCCAGATGTAGCCTTTGTACCTCTAGGAATGACGGATTATTTAGTCATC
     I  Y  I  Y  V  P  D  P  D  V  A  F  V  P  L  G  M  T  D  Y  L  V  I

622 GTGGAGGATGATGATTCTGCCATTATACCTTGTCGCACAACTGATCCCGAGACTCCTGTAACCTTACAC
     V  E  D  D  D  S  A  I  I  P  C  R  T  T  D  P  E  T  P  V  T  L  H

691 AACAGTGAGGGGGTGGTACCTGCCTCCTACGACAGCAGACAGGGCTTTAATGGGACCTTCACTGTAGGG
     N  S  E  G  V  V  P  A  S  Y  D  S  R  Q  G  F  N  G  T  F  T  V  G

760 CCCTATATCTGTGAGGCCACCGTCAAAGGAAAGAAGTTCCAGACCATCCCATTTAATGTTTATGCTTTA
     P  Y  I  C  E  A  T  V  K  G  K  K  F  Q  T  I  P  F  N  V  Y  A  L

829 AAAGCAACATCAGAGCTGGATCTAGAAATGGAAGCTCTTAAAACCGTGTATAAGTCAGGGGAAACGATT
     K  A  T  S  E  L  D  L  E  M  E  A  L  K  T  V  Y  K  S  G  E  T  I

898 GTGGTCACCTGTGCTGTTTTTAACAATGAGGTGGTTGACCTTCAATGGACTTACCCTGGAGAAGTGAAA
     V  V  T  C  A  V  F  N  N  E  V  V  D  L  Q  W  T  Y  P  G  E  V  K
```

Fig. 1B

```
 967 GGCAAAGGCATCACAATACTGGAAGAAATCAAAGTCCCATCCATCAAATTGGTGTACACTTTGACGGTC
      G  K  G  I  T  I  L  E  E  I  K  V  P  S  I  K  L  V  Y  T  L  T  V

1036 CCCGAGGCCACGGTGAAAGACAGTGGAGATTACGAATGTGCTGCCCGCCAGGCTACCAGGGAGGTCAAA
      P  E  A  T  V  K  D  S  G  D  Y  E  C  A  A  R  Q  A  T  R  E  V  K

1105 GAAATGAAGAAAGTCACTATTTCTGTCCATGAGAAAGGTTTCATTGAAATCAAACCCACCTTCAGCCAG
      E  M  K  K  V  T  I  S  V  H  E  K  G  F  I  E  I  K  P  T  F  S  Q

1174 TTGGAAGCTGTCAACCTGCATGAAGTCAAACATTTTGTTGTAGAGGTGCGGGCCTACCCACCTCCCAGG
      L  E  A  V  N  L  H  E  V  K  H  F  V  V  E  V  R  A  Y  P  P  R

1243 ATATCCTGGCTGAAAAACAATCTGACTCTGATTGAAAATCTCACTGAGATCACCACTGATGTGGAAAAG
      I  S  W  L  K  N  N  L  T  L  I  E  N  L  T  E  I  T  T  D  V  E  K

1312 ATTCAGGAAATAAGGTATCGAAGCAAATTAAAGCTGATCCGTGCTAAGGAAGAAGACAGTGGCCATTAT
      I  Q  E  I  R  Y  R  S  K  L  K  L  I  R  A  K  E  E  D  S  G  H  Y

1381 ACTATTGTAGCTCAAAATGAAGATGCTGTGAAGAGCTATACTTTTGAACTGTTAACTCAAGTTCCTTCA
      T  I  V  A  Q  N  E  D  A  V  K  S  Y  T  F  E  L  L  T  Q  V  P  S

1450 TCCATTCTGGACTTGGTCGATGATCACCATGGCTCAACTGGGGGACAGACGGTGAGGTGCACAGCTGAA
      S  I  L  D  L  V  D  D  H  H  G  S  T  G  G  Q  T  V  R  C  T  A  E

1519 GGCACGCCGCTTCCTGATATTGAGTGGATGATATGCAAAGATATTAAGAAATGTAATAATGAAACTTCC
      G  T  P  L  P  D  I  E  W  M  I  C  K  D  I  K  K  C  N  N  E  T  S

1588 TGGACTATTTTGGCCAACAATGTCTCAAACATCATCACGGAGATCCACTCCCGAGACAGGAGTACCGTG
      W  T  I  L  A  N  N  V  S  N  I  I  T  E  I  H  S  R  D  R  S  T  V

1657 GAGGGCCGTGTGACTTTCGCCAAAGTGGAGGAGACCATCGCCGTGCGATGCCTGGCTAAGAATCTCCTT
      E  G  R  V  T  F  A  K  V  E  E  T  I  A  V  R  C  L  A  K  N  L  L

1726 GGAGCTGAGAACCGAGAGCTGAAGCTGGTGGCTCCCACCCTGCGTTCTGAACTCACGGTGGCTGCTGCA
      G  A  E  N  R  E  L  K  L  V  A  P  T  L  R  S  E  L  T  V  A  A  A

1795 GTCCTGGTGCTGTTGGTGATTGTGATCATCTCACTTATTGTCCTGGTTGTCATTTGGAAACAGAAACCG
      V  L  V  L  L  V  I  V  I  I  S  L  I  V  L  V  V  I  W  K  Q  K  P
```

Fig. 1C

```
1864 AGGTATGAAATTCGCTGGAGGGTCATTGAATCAATCAGCCCGGATGGACATGAATATATTTATGTGGAC
      R  Y  E  I  R  W  R  V  I  E  S  I  S  P  D  G  H  E  Y  I  Y  V  D

1933 CCGATGCAGCTGCCTTATGACTCAAGATGGGAGTTTCCAAGAGATGGACTAGTGCTTGGTCGGGTCTTG
      P  M  Q  L  P  Y  D  S  R  W  E  F  P  R  D  G  L  V  L  G  R  V  L

2002 GGGTCTGGAGCGTTTGGGAAGGTGGTTGAAGGAACAGCCTATGGATTAAGCCGGTCCCAACCTGTCATG
      G  S  G  A  F  G  K  V  V  E  G  T  A  Y  G  L  S  R  S  Q  P  V  M

2071 AAAGTTGCAGTGAAGATGCTAAAACCCACGGCCAGATCCAGTGAAAAACAAGCTCTCATGTCTGAACTG
      K  V  A  V  K  M  L  K  P  T  A  R  S  S  E  K  Q  A  L  M  S  E  L

2140 AAGATAATGACTCACCTGGGGCCACATTTGAACATTGTAAACTTGCTGGGAGCCTGCACCAAGTCAGGC
      K  I  M  T  H  L  G  P  H  L  N  I  V  N  L  L  G  A  C  T  K  S  G

2209 CCCATTTACATCATCACAGAGTATTGCTTCTATGGAGATTTGGTCAACTATTTGCATAAGAATAGGGAT
      P  I  Y  I  I  T  E  Y  C  F  Y  G  D  L  V  N  Y  L  H  K  N  R  D

2278 AGCTTCCTGAGCCACCACCCAGAGAAGCCAAAGAAAGAGCTGGATATCTTTGGATTGAACCCTGCTGAT
      S  F  L  S  H  H  P  E  K  P  K  K  E  L  D  I  F  G  L  N  P  A  D

2347 GAAAGCACACGGAGCTATGTTATTTTATCTTTTGAAAACAATGGTGACTACATGGACATGAAGCAGGCT
      E  S  T  R  S  Y  V  I  L  S  F  E  N  N  G  D  Y  M  D  M  K  Q  A

2416 GATACTACACAGTATGTCCCCATGCTAGAAAGGAAAGAGGTTTCTAAATATTCCGACATCCAGAGATCA
      D  T  T  Q  Y  V  P  M  L  E  R  K  E  V  S  K  Y  S  D  I  Q  R  S

2485 CTCTATGATCGTCCAGCCTCATATAAGAAGAAATCTATGTTAGACTCAGAAGTCAAAAACCTCCTTTCA
      L  Y  D  R  P  A  S  Y  K  K  K  S  M  L  D  S  E  V  K  N  L  L  S

2554 GATGATAACTCAGAAGGCCTTACTTTATTGGATTTGTTGAGCTTCACCTATCAAGTTGCCCGAGGAATG
      D  D  N  S  E  G  L  T  L  L  D  L  L  S  F  T  Y  Q  V  A  R  G  M

2623 GAGTTTTTGGCTTCAAAAAATTGTGTCCACCGTGATCTGGCTGCTCGCAACGTCCTCCTGGCACAAGGA
      E  F  L  A  S  K  N  C  V  H  R  D  L  A  A  R  N  V  L  L  A  Q  G

2692 AAAATTGTGAAGATCTGTGACTTTGGCCTGGCCAGAGACATCATGCATGATTCGAACTATGTGTCGAAA
      K  I  V  K  I  C  D  F  G  L  A  R  D  I  M  H  D  S  N  Y  V  S  K

2761 GGCAGTACCTTTCTGCCCGTGAAGTGGATGGCTCCTGAGAGCATCTTTGACAACCTCTACACCACACTG
      G  S  T  F  L  P  V  K  W  M  A  P  E  S  I  F  D  N  L  Y  T  T  L
```

Fig. 1D

```
2830 AGTGATGTCTGGTCTTATGGCATTCTGCTCTGGGAGATCTTTTCCCTTGGTGGCACCCCTTACCCCGGC
      S  D  V  W  S  Y  G  I  L  L  W  E  I  F  S  L  G  G  T  P  Y  P  G

2899 ATGATGGTGGATTCTACTTTCTACAATAAGATCAAGAGTGGGTACCGGATGGCCAAGCCTGACCACGCT
      M  M  V  D  S  T  F  Y  N  K  I  K  S  G  Y  R  M  A  K  P  D  H  A

2968 ACCAGTGAAGTCTACGAGATCATGGTGAAATGCTGGAACAGTGAGCCGGAGAAGAGACCCTCCTTTTAC
      T  S  E  V  Y  E  I  M  V  K  C  W  N  S  E  P  E  K  R  P  S  F  Y

3037 CACCTGAGTGAGATTGTGGAGAATCTGCTGCCTGGACAATATAAAAAGAGTTATGAAAAAATTCACCTG
      H  L  S  E  I  V  E  N  L  L  P  G  Q  Y  K  K  S  Y  E  K  I  H  L

3106 GACTTCCTGAAGAGTGACCATCCTGCTGTGGCACGCATGCGTGTGGACTCAGACAATGCATACATTGGT
      D  F  L  K  S  D  H  P  A  V  A  R  M  R  V  D  S  D  N  A  Y  I  G

3175 GTCACCTACAAAAACGAGGAAGACAAGCTGAAGGACTGGGAGGGTGGTCTGGATGAGCAGAGACTGAGC
      V  T  Y  K  N  E  E  D  K  L  K  D  W  E  G  G  L  D  E  Q  R  L  S

3244 GCTGACAGTGGCTACATCATTCCTCTGCCTGACATTGACCCTGTCCCTGAGGAGGAGGACCTGGGCAAG
      A  D  S  G  Y  I  I  P  L  P  D  I  D  P  V  P  E  E  E  D  L  G  K

3313 AGGAACAGACACAGCTCGCAGACCTCTGAAGAGAGTGCCATTGAGACGGGTTCCAGCAGTTCCACCTTC
      R  N  R  H  S  S  Q  T  S  E  E  S  A  I  E  T  G  S  S  S  T  F

3382 ATCAAGAGAGAGGACGAGACCATTGAAGACATCGACATGATGGACGACATCGGCATAGACTCTTCAGAC
      I  K  R  E  D  E  T  I  E  D  I  D  M  M  D  D  I  G  I  D  S  S  D

3451 CTGGTGGAAGACAGCTTCCTGTAACTGGCGGATTCGAGGGGTTCCTTCCACTTCTGGGGCCACCTCTGG
      L  V  E  D  S  F  L
                       1089

3520 ATCCCGTTCAGAAAACCACTTTATTGCAATGCGGAGGTTGAGAGGAGGACTTGGTTGATGTTTAAAGAG
3589 AAGTTCCCAGCCAAGGGCCTCGGGGAGCGTTCTAAATATGAATGAATGGGATATTTTGAAATGAACTTT
3658 GTCAGTGTTGCCTCTTGCAATGCCTCAGTAGCATCTCAGTGGTGTGTGAAGTTTGGAGATAGATGGATA
3727 AGGGAATAATAGGCCACAGAAGGTGAACTTTGTGCTTCAAGGACATTGGTGAGAGTCCAACAGACACAA
3796 TTTATACTGCGACAGAACTTCAGCATTGTAATTATGTAAATAACTCTAACCAAGGCTGTGTTTAGATTG
3865 TATTAACTATCTTCTTTGGACTTCTGAAGAGACCACTCAATCCATCCTGTACTTCCCTCTTGAAACCTG
3934 ATGTAGCTGCTGTTGAACTTTTTAAAGAAGTGCATGAAAAACCATTTTTGAACCTTAAAAGGTACTGGT
4003 ACTATAGCATTTTGCTATCTTTTTTAGTGTTAAAGAGATAAAGAATAATAAG
```

PDGF α RECEPTOR

Cross-Reference to Related Application

This application is a continuation of U.S. application Ser. No. 07/355,018, filed May 22, 1989, now abandoned.

TECHNICAL FIELD

The present invention relates to biological receptors and their use. More specifically, the invention provides a novel receptor for platelet-derived growth factor (PDGF) and methods for using the receptor to identify PDGF agonists and antagonists.

BACKGROUND OF THE INVENTION

In higher eukaryotic cells, the interaction between ligands (e.g., peptide hormones, growth factors and their analogs) and their receptors is of central importance in the transmission of and response to a variety of extracellular signals. It is generally accepted that peptide hormones and growth factors elicit their biological functions by binding to specific recognition sites (receptors) on the plasma membranes of the target cells. Upon ligand binding, the receptors are believed to undergo a conformational change, triggering intra-cellular responses, which in turn result in the activation or inhibition of some cellular process(es). Ligand analogs fall into two classes: those that mimic the effect(s) of the corresponding natural ligand, termed agonists; and those that block receptor-ligand binding or the effects elicited by the natural ligand, termed antagonists.

Of particular interest is the interaction between platelet-derived growth factor (PDGF) and its receptor(s). PDGF is the major mitogenic protein in serum for mesenchymal cells. It induces cell multiplication or DNA synthesis in cultured smooth muscle cells, fibroblasts and glial cells, is a potent chemoattractant and exhibits other biological activities. The biology of PDGF is reviewed by Ross et al. (Cell 46: 155-169, 1986). PDGF has been shown to play an important role in the wound-healing response (Ross and Glomset, *New Eng. J. Med.* 295: 369, 1976; Grotendorst et al. *J. Clin. Invest.* 76: 2323-2329, 1985; Murray et al., U.S. Pat. application Ser. No. 230,190) and is believed to play a causative role in the development of the proliferative lesions of atherosclerosis (Ross and Glomset, ibid.). These activities are mediated by the binding of PDGF to membrane-associated receptors comprising an extracellular binding site, a transmembrane anchor and an intracellular tyrosine kinase domain. Antagonists that block receptors against the action of endogenous PDGF may be useful in the treatment of atherosclerosis or in the inhibition of other conditions involving PDGF-induced aberrant growth patterns. PDGF agonists may be useful for promoting wound healing.

Current methods for screening potential agonists and antagonists involve assaying the binding of radiolabeled compounds to responsive cells, to the membrane fractions of disrupted cells, or to solubilized receptors. Alternatively, compounds may be screened for their ability to compete with a labeled known ligand for cell-surface receptors. For example, Lefkowitz et al. (*Biochem. Biophys. Res. Comm.* 60: 703-709, 1974), Aurbach et al. (*Science* 186: 1223-1225, 1974) and Atlas et al. (*Proc. Natl. Acad. Sci. USA* 71: 4246-4248, 1974) disclose receptor-binding assays for β-adrenergic agonists and antagonists. These assays utilize isolated erythrocyte membranes.

The success of current screening procedures depends in part on the availability of reproducibly high quality preparations of membrane fractions or receptor molecules. The preparation of membrane fractions and soluble receptor molecules often involves extensive manipulations and complex purification steps. Receptors, being integral membrane proteins, require cumbersome purification procedures that include the use of detergents and other solvents that interfere with their biological activity. Furthermore, the large size of typical receptor molecules makes them particularly vulnerable to proteolysis during purification. Production of large amounts of functional receptor proteins by standard techniques of protein chemistry is not economical. The use of membrane preparations in ligand binding assays typically results in low reproducibility due to the variability of such preparations.

In the case of growth factor receptors, ligand-binding assays generally require the isolation of responsive cell lines. Often only a limited population of a responsive cell type is responsive to a particular agent, and such cells may be responsive only under certain conditions. In addition, these cells may be difficult to grow in culture or may possess a low number of receptors.

Most currently available cell types responsive to PDGF contain only a low number of receptors per cell, thus requiring large numbers of cells to assay potential PDGF analogs or antagonists. Such assays are labor-intensive and complex, and do not readily lend themselves to automation and high through-put.

A PDGF receptor that specifically binds the PDGF BB isoform at high affinity (hereinafter referred to as the β-receptor) has been described (Claesson-Walsh et al., *Mol. Cell. Biol.* 8: 3476-3486, 1988; Gronwald et al., *Proc. Natl. Acad. Sci. USA* 85: 3435-3439, 1988). Because PDGF can exist in any of three isoforms (AA, AB and BB) or mixtures thereof, this receptor cannot be used to detect all forms of PDGF or analogs thereof.

There is therefore a need in the art for an assay system that permits commercial scale screening of compounds for PDGF agonist and antagonist activity. Such an assay system should be rapid, inexpensive, adaptable to high through-put screening and capable of detecting analogs of all PDGF isoforms. The present invention provides such assay systems, and further provides other related advantages.

DISCLOSURE OF THE INVENTION

The present invention provides an isolated DNA molecule encoding a PDGF receptor comprising the amino acid sequence shown in FIG. 1 from leucine, amino acid number 20, to leucine, amino acid number 1089. In one embodiment, the DNA molecule encodes the amino acid sequence shown in FIG. 1 from methionine, amino acid number 1, to leucine, amino acid number 1089. The DNA molecule may comprise the nucleotide sequence shown in FIG. 1 from nucleotide number 262 to nucleotide number 3471, or from nucleotide number 205 to nucleotide number 3471.

In a related aspect, the present invention provides cells transfected or transformed with a DNA construct comprising a transcriptional promoter operably linked to a DNA molecule as described above. In certain embodiments of the invention, the cells are cultured mammalian cells or yeast cells.

In another aspect, the transfected or transformed cells expressing the PDGF receptor as a cell surface protein are used within methods for detecting PDGF agonist or antagonist activity in a test compound. In one embodiment the methods include incubating the cells with the test compound under conditions suitable for the binding of PDGF to the receptor; incubating the cells in the presence of PDGF coupled to a label capable of providing a detectable signal, concurrent with or subsequent to incubating the cells with the test compound; and detecting binding of the labeled PDGF to the receptor as an indicator of PDGF agonist or antagonist activity in the test compound. The methods may further include the step of detecting PDGF-like mitogenic activity in the test compound, such as by measuring incorporation of thymidine by the cells in the presence of the test compound.

These and other embodiments of the invention will become evident upon reference to the following detailed description and attached drawings.

BRIEF DESCRIPTION OF THE DRAWINGS

FIG. 1 illustrates the sequence of the PDGF α-receptor cDNA and the amino acid sequence (using standard one-letter codes) encoded by the cDNA. Numbers at the ends of lines refer to nucleotide positions. Numbers below the sequence refer to amino acid positions.

BEST MODE FOR CARRYING OUT THE INVENTION

Figure 2:
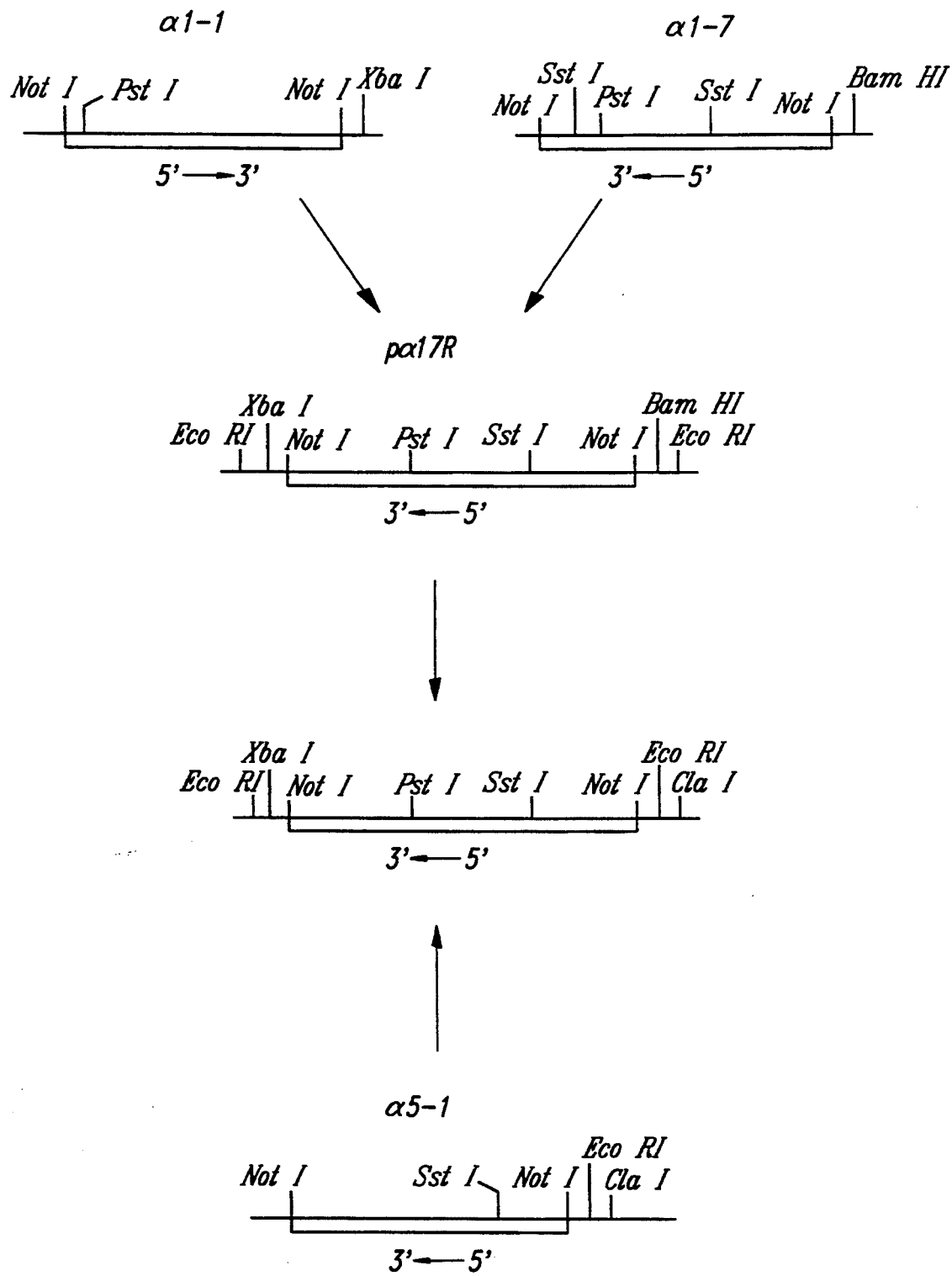
FIG. 2 illustrates the assembly of a cDNA molecule encoding the PDGF α-receptor. cDNA sequences are shown as open boxes. Vector sequences are shown as lines. Only those portions of the vectors adjacent to the cDNA inserts are shown.

Prior to setting forth the invention, it may be useful to define certain terms to be used hereinafter:

DNA construct: A DNA molecule, or a clone of such a molecule, either single- or double-stranded, which has been modified through human intervention to contain segments of DNA combined and juxtaposed in a manner that as a whole would not otherwise exist in nature.

Transfection and transformation: The process of altering the genotype of a recipient cell or microorganism by the introduction of cloned DNA. "Transfection" refers to the insertion of DNA into cultured mammalian cells. "Transformation" is used to describe the insertion of DNA into other cell types, including fungi and bacteria.

PDGF: As used herein, the term "PDGF" includes the AA, AB, and BB isoforms of platelet-derived growth factor individually or in any combination, regardless of source.

Receptor: A cellular or cell surface protein that binds a particular ligand or group of ligands with high affinity. In its native state, a receptor is membrane-associated, generally includes external, transmembrane and cytoplasmic domains and is capable of signal transmission. As used herein, the term "PDGF receptor" refers to a receptor that specifically binds any or all of the isoforms of PDGF.

The present invention provides a novel PDGF receptor, termed the "α-receptor", which may be used to screen compounds for PDGF agonist and antagonist activities. The PDGF α-receptor described herein is similar biochemically to the previously-described PDGF β-receptor. Similar features include high affinity binding of PDGF BB homodimer, ability to stimulate mitogenesis upon ligand binding, and autophosphorylation of tyrosine residues within the intracellular portion of the molecule upon ligand binding. Analysis of the amino acid sequence predicted on the basis of the cDNA sequence (FIG. 1) indicates that the α-receptor is a member of the split tyrosine kinase receptor family, as are the PDGF β-receptor, the CSF-1 receptor and the C-kit gene product.

The PDGF α-receptor is distinguished from the previously-described PDGF β-receptor on the basis of several properties. For instance, the α-receptor is able to bind the AA, AB and BB isoforms of PDGF with high affinity. In contrast, the β-receptor binds only the BB isoform with high affinity and, to some extent, the AB isoform. Although similar in size, the mature, cell-surface forms of the α- and β-receptors can be distinguished on polyacrylamide gels under reducing conditions. The α-receptor has an apparent molecular weight of approximately 180,000 daltons, whereas the β-receptor has an apparent molecular weight of approximately 185,000 daltons. The two receptors are also distinguishable by amino acid sequence.

The PDGF α-receptor of the present invention may be prepared by transfecting or transforming host cells to express a DNA sequence encoding the receptor. The receptor may then be isolated from the cells or the cells themselves may be used within assays for detecting PDGF agonists and antagonists as described below.

A DNA molecule encoding the human PDGF α-receptor is isolated from a library of human genomic or cDNA sequences. Such libraries are prepared by standard procedures, such as those disclosed by Gubler and Hoffman (*Gene* 25: 263–269, 1983). It is preferred that the molecule is a cDNA molecule because cDNA lacks introns and is therefore more suited to manipulation and expression in transfected or transformed cells. A preferred source of mRNA for use in preparation of a cDNA library is the MG-63 human osteosarcoma cell line (available from ATCC under accession number CRL 1427). The MG-63 cell line has been found to contain approximately equivalent numbers of PDGF α-and β-receptors on its cell surface as determined by ligand-binding studies. Saturation binding experiments with $^{125}$I-PDGF BB and $^{125}$I-PDGF AB indicate that approximately 50,000 binding sites for each receptor type are present on the surfaces of these cells. Alternatively, other PDGF-responsive cell types, such as human diploid fibroblasts, may be used. The mRNA is isolated from the cells and cDNA is prepared and cloned in a suitable vector, such as the bacteriophage λgt10 (ATCC 40179; commercially available from Bethesda Research Laboratories, Gaithersburg, Md., or Invitrogen, San Diego, Calif.). As described in detail hereinafter, a cDNA library prepared from MG-63 RNA was screened with a cDNA probe containing sequences encoding the cytoplasmic portion of the PDGF β-receptor, and the blots were washed under increasingly stringent conditions. α-receptor sequences were found to hybridize to this probe at low stringency but to be distinguishable from β-receptor sequences by their inability to remain hybridized to the probe under more stringent wash conditions, which require sequence identity for hybridization. Alternatively, human PDGF α-receptor sequences disclosed herein may be used as probes. Positive clones are analyzed by restriction enzyme mapping and nucleotide sequence analysis. Screening and analysis are repeated until clones representing the entire receptor coding sequence are obtained.

Once the complete DNA sequence has been obtained, it is inserted into an expression vector. The expression vector contains a promoter operably linked to the DNA sequence. Other genetic elements may also be included in the vector, the selection of which is based on the particular host cells with which the vector is to be used. These genetic elements include terminators, enhancers, polyadenylation signals, RNA splicing signals, leaders and selectable markers. Expression vectors will also commonly contain one or more origins of replication. Many examples of each element are known and available, and the selection of a proper combination of elements is within the ordinary level of skill in the art.

Expression vectors as described above are used to transfect or transform eukaryotic host cells. Suitable cells include yeast cells, particularly the yeast *Saccharomyces cerevisiae*, and cultured mammalian cells, such as baby hamster kidney cells. Methods for transforming yeast cells are described by Beggs (*Nature* 275: 104–108, 1978) and Hinnen et al. (*Proc. Natl. Acad. Sci. USA* 75: 1929–1933, 1978). Methods for transfecting mammalian cells are disclosed by Graham and van der Eb (*Virol.* 52: 456, 1973), Wigler et al. (*Cell* 14: 725, 1978) and Neumann et al. (*EMBO J.* 1: 841–845, 1982). Preferred mammalian cell lines include baby hamster kidney (BHK) cell lines, such as the tk⁻ts13 BHK cell line disclosed by Waechter and Baserga (*Proc. Natl. Acad. Sci. USA* 79:1106–1110, 1982), hereinafter referred to as "BHK 570." It is generally preferred that the host cells do not express endogenous PDGF β-receptor or express β-receptor at only a low level. Such cells, when transfected or transformed to express the α-receptor, may be used to specifically assay for α-receptor ligands. However, cells expressing higher quantities of β-receptor may also be transfected to express the α-receptor, thus providing cells capable of expressing all classes of PDGF receptors.

The transfected or transformed cells are then screened for the ability to bind PDGF and/or anti-αreceptor antibodies. Those cells expressing sufficiently high numbers of cell surface PDGF α-receptors (generally at least 4–5×10⁵ receptors per cell, preferably at least about 1×10⁶ receptors/cell) may be used in assay systems for agonist and antagonist screening.

PDGF α-receptor protein may be purified from the recombinant cells by solubilizing the cells in a suitable detergent (e.g., Tween ™ [polyoxyethylenesorbitan]or Triton ™, available from Sigma Chemical Co., St. Louis, Mo.) to prepare a membrane extract. The receptor protein is then isolated by immunoaffinity using an anti-receptor antibody bound to a solid support, generally in the form of a column. Alternatively, the receptor protein may be produced in a fused form with a peptide for which an antibody is available. The fusion protein is then isolated using an anti-peptide antibody, and the peptide is enzymatically removed from the receptor protein, for example as disclosed in U.S. Pat. Nos. 4,703,004 and 4,782,137. An anti-peptide antibody is commercially available from Immunex Corp. (Seattle, Wash.). Chemical purification methods commonly used in the art for isolating membrane proteins may also be used.

Assay systems provided by the present invention may be used to screen compounds for PDGF agonist and antagonist activity. Briefly, the transfected or transformed cells expressing cell-surface PDGF α-receptor are cultured in an appropriate growth medium to the desired cell density. Binding assays are then carried out under conditions determined to be suitable for binding of PDGF to the cell-associated α-receptor. Determination of suitable conditions is within the level of ordinary skill in the art. Generally, assays are performed in the absence of serum to avoid contamination with serum-borne growth factors. A preferred assay medium for use with transfected mammalian cells is Ham's F12 (available from GIBCO, Grand Island, N.Y.) containing 25 mM Hepes, pH 7.4, 0.25% serum albumin and antibiotics. Binding of test compounds is then assayed using known methods, for example that of Hart et al. (*J. Biol. Chem.* 262:10780–10785, 1987). The cells are incubated with the test compound, and PDGF, coupled to a radioisotope or other label capable of producing a detectable signal, is subsequently added. Preferred labels include $^{125}$I and other radioisotopes, although it will be appreciated that fluorescent labels, biotin and enzymes commonly used in the art may also be employed. Alternatively, the test compound and PDGF are added concurrently. The amount of PDGF bound to the cells is then measured and compared to PDGF binding in control (minus test compound) cultures. A reduction in PDGF binding compared to the control culture indicates that the test compound binds to the α-receptor. Compounds that bind the receptor are then distinguished as PDGF agonists or antagonists by assaying for PDGF-like mitogenic activity (i.e., mitogenesis or receptor phosphorylation). A preferred mitogenesis assay, described by Raines and Ross (*Methods Enzymol.* 109:749–773, 1985), measures the uptake of $^3$H-thymidine by mitogen-stimulated cells. Briefly, the test compound is added to quiescent cultures of cells transfected or transformed to express the PDGF α-receptor. The test compound is then removed and $^3$H-thymidine is added. Incorporation of labeled thymidine into DNA is indicative of PDGF or PDGF agonist binding. Receptor phosphorylation may be assayed as disclosed by Hart et al. (*Science* 240:1529–1531, 1988) by incubating receptor-containing membrane extracts with [γ-$^{32}$P] ATP in the presence of the test compound. The extracts are analyzed for receptor phosphorylation by gel electrophoresis and autoradiography.

The above-described assays are preferably carried out in 96-well microtiter plates. These plates are commercially available and may be used within automated assay systems.

PDGF agonists identified in these assays are suitable for use within therapeutic compositions for enhancing the wound-healing process in warm-blooded animals. Examples of wounds that may be treated with PDGF agonists include burns, chronic non-healing dermal ulcers, superficial wounds and lacerations, abrasions and surgical wounds.

Therapeutic compositions may be prepared by combining PDGF agonists with suitable carriers, as well as adjuvants, diluents, or stabilizers. Suitable adjuvants include collagen or hyaluronic acid preparations, fibronectin, factor XIII, polyethylene glycol, or other proteins or substances designed to stabilize or otherwise enhance the active therapeutic ingredient(s). Diluents include albumins, saline, sterile water, etc. Other stabilizers, antioxidants, or protease inhibitors may also be added. Alternatively, PDGF agonists may be applied to wound dressings as aqueous solutions. These therapeutic compositions may be reapplied at one- to several-day intervals until healing is complete.

These therapeutic compositions may also contain other pharmaceutically active ingredients, for example heparin, which has been shown to accelerate the healing of thermal burns. Other growth factors such as TGF-$\alpha$, TGF-$\beta$, EGF, FGF, platelet factor 4, insulin or somatomedins (see Grotendorst et al., *J. Clin. Invest.* 76:2323-2329, 1985) and angiogenesis factors, may also work synergistically with the PDGF analogs. Antibiotics may also be included to keep the wound free of infection.

Therapeutic compositions containing PDGF antagonists may be formulated in suitable carriers or diluents and administered in cases where it is desirable to block the effects of endogenous PDGF, for example in treatment of atherosclerosis or fibrotic diseases.

The following detailed example is offered by way of illustration, not by way of limitation.

EXAMPLE

A. cDNA Construction

RNA was prepared by the method of Chirgwin et al. (*Biochemistry* 18: 5294, 1979) and twice purified on oligo dT cellulose to yield poly (A)+RNA.

cDNA was prepared in $\lambda$gt10 phage using a kit purchased from Invitrogen (San Diego, Calif). The resulting $\lambda$ phage DNAs were packaged with a coat particle mixture from Stratagene (La Jolla, Calif.), infected into *E. coli* strain C600 Hfl−, and titered.

B. Library Screening

Approximately $1.4 \times 10^6$ phage recombinants were plated to produce plaques for screening. Nitrocellulose filter lifts were made according to standard methods and hybridized to a $\beta$-receptor DNA fragment (Gronwald et al., ibid.) labeled with $^{32}$P. The probe fragment was the 1.9 kb Fsp I-Hind III segment that encompasses the transmembrane and cytoplasmic domain coding portions of the PDGF $\beta$-receptor cDNA. Hybridization was performed for 36 hours at 42° C. in a mixture containing 40% formamide, 5×SSCP (SSC containing 25 mM phosphate buffer, pH 6.5), 200 ug/ml denatured salmon sperm DNA, 3×Denhardt's, and 10% dextran sulfate. Following hybridization, the filters were washed extensively at room temperature in 2×SSC, then for 15 minutes at 47°–48° C. Following exposure overnight to X-ray film, the filters were treated to increasingly stringent washes followed by film recording until a final treatment at 0.1×SSC, 65° C. was reached.

Film analysis indicated that a "family" of plaques hybridized at lower wash stringency to the probe but were not seen at the highest stringency employed. This group of clones was selected for further analysis.

C. Clone Analysis

Two $\lambda$ phage clones obtained from the initial screening were subcloned into the Not I site of a pUC-type plasmid vector (pBluescript SK+, obtained from Stratagene, La Jolla, Calif.) and analyzed by restriction mapping and sequence analysis.

Restriction enzyme analysis of a phage clone designated $\alpha$1-1 revealed a restriction fragment pattern dissimilar from that of the $\beta$-receptor with the exception of a common Bgl II-Bgl II band of approximately 160 bp. The $\beta$-receptor contains two similarly spaced Bgl II sites within the region coding for the second tyrosine kinase domain.

Sequence data obtained from the ends of $\alpha$1-1 allowed a putative orientation and alignment of the cDNA with the $\beta$-receptor gene. Sequence obtained from the ~300 bases at one terminus showed no clear homology to the $\beta$-receptor. This region came to be understood to be 3' non-coding sequences of the cloned cDNA. Sequence obtained from the opposite end of $\alpha$1-1 was found to contain an open reading frame, portions of which were highly homologous to the PDGF $\beta$-receptor, and to a far lesser extent, the C-fms and C-kit genes. Alignment of the $\alpha$1-1 open reading frame and PDGF $\beta$-receptor amino acid sequence revealed that $\alpha$1-1 contained at its 5' end approximately 13 amino acid codons of the extracellular domain followed by a highly hydrophobic transmembrane domain. This initial sequence analysis revealed a striking homology to the PDGF $\beta$-receptor amino acid sequence in the cytoplasmic portion between the membrane spanning region and the first tyrosine kinase domain. Of the 46 amino acids found in this portion (domain), 38 are identical and the changes are largely conservative ones. This 85% amino acid identity is mimicked to a lesser extent in the membrane spanning region (48%) but is not found in the small amount of protein sequence extrapolated from the 5' most sequences found in $\alpha$1-1.

Restriction analysis of a second plasmid subclone (designated $\alpha$1-7) revealed an overlap of the 5'~1.2 kb of clone $\alpha$1-1, and an additional ~2.2 kb of sequence extending in the 5' direction. Sequence analysis revealed that this clone has at its 3' end the coding sequence for the second tyrosine kinase domain, which contains regions of near sequence identity to the corresponding regions in the PDGF $\beta$-receptor. The 5' end of clone $\alpha$1-7 contained non-receptor sequences.

Two additional $\alpha$-receptor clones were obtained by probing with $\alpha$1-1 sequences. Clone $\alpha$1-1 was digested with Not I and Spe I, and a 230 bp fragment was recovered. $\alpha$1-1 was also digested with Bam HI and Not I, and a 550 bp fragment was recovered. A clone that hybridized to the 230 bp probe was designated $\alpha$5-1. This clone contained the 5'-most coding sequence for the receptor. Another clone, designated $\alpha$6-3, hybridized to the 550 bp probe and was found to contain 3' coding and noncoding sequences, including the poly(A) tail.

Clone $\alpha$1-1 was radio-labeled ($^{32}$P) and used to probe a northern blot (Thomas, *Methods Enzymol.* 100:225-265, 1983) of the MG-63 poly (A)+RNA used to prepare the cDNA library. A single band of ~6.6 kb was observed.

RNAs from several other cell lines for which information was known regarding PDGF $\alpha$-receptor protein expression were probed by northern format with $\alpha$1-1 cDNA. Receptor-positive cell lines tested included the human fibroblast SK4, WI-38 and 7573 lines; the mouse fibroblast line DI 3T3; the U2-OS human osteosarcoma cell line and baboon aortic smooth muscle cells. Negative lines included A431 (an epithelial cell line) and VA 13 (SV40-transformed WI-38 cells). In all cases, the amount of the 6.6 kb band detected in these RNAs correlated well with the relative levels of $\alpha$-receptor detected on the respective cell surfaces. The 6.6 kb RNA was not detected in RNA preparations from any cell lines of hematopoietic origin analyzed, in agreement with a lack of PDGF $\alpha$-receptor protein detected on these cell types.

Clones α1-1 and α1-7 were joined at a unique Pst I site in the region encoding the transmembrane portion of the receptor. Clone α1-1 was digested with Pst I and Xba I and the receptor sequence fragment was recovered. Clone α1-7 was digested with Pst I and Bam HI and the receptor fragment was recovered. The two fragments were ligated with Xba I+ Bam HI-digested pIC19R (Marsh et al. Gene 32: 481–486, 1984) to construct plasmid pα17R (FIG. 2).

The remainder of the 5'-most α-receptor sequence was obtained from clone α5-1 as an Sst I-Cla I fragment. This fragment was joined to the Eco RI-Sst I receptor fragment of pα17R and cloned into Eco RI+Cla I-digested pBluescript SK+plasmid to construct plasmid pα17B (FIG. 2).

The three cDNA fragments used in the construction of pα17B were cloned in the phage vectors M13mp18 and M13mp19. The cDNA fragments were sequenced by the method of Sanger et al. (*Proc. Natl. Acad. Sci. USA* 74:5463–5467, 1977). The cDNA sequence and the deduced amino acid sequence are shown in FIG. 1. The coding sequence begins at nucleotide 205 of the cloned cDNA. Based on the model of von Heijne et al. (*Nuc. Acids Res.* 14:4683–4690, 1986) signal peptide cleavage is predicted to occur after amino acid 19 (serine), resulting in a 1070 amino acid mature protein.

D. Expression Vector Construction and Transfection

Figure 3:
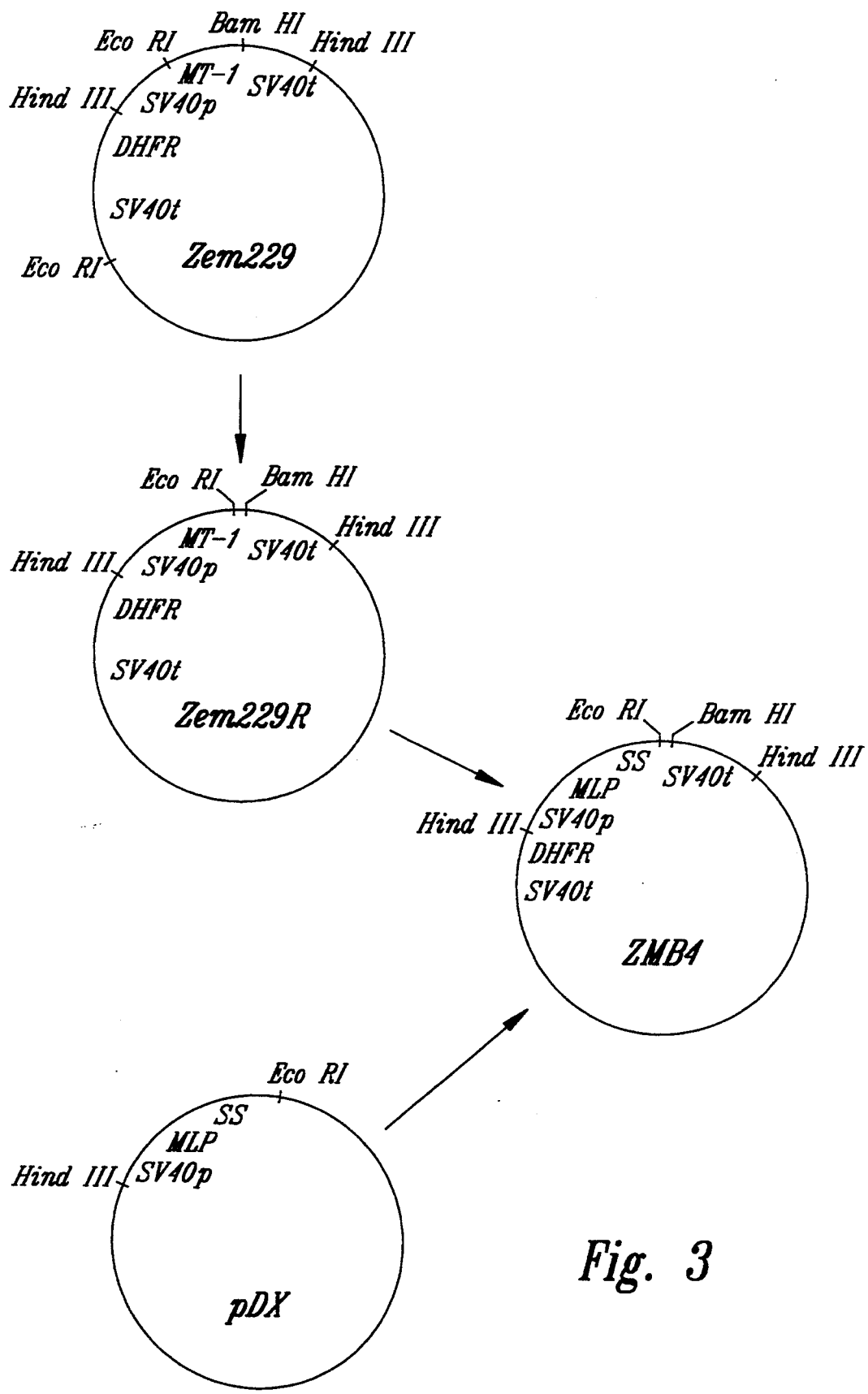
FIG. 3 illustrates the construction of the vector ZMB4. Symbols used are: DHFR, mouse dihydrofolate reductase gene; SV40p, SV40 promoter; SV40t, SV40 terminator; MT-1, mouse metallothionein-1 promoter; MLP, adenovirus 2 major late promoter; and SS, splicing signals.

A vector for expressing the α-receptor in mammalian cells was then constructed. Zem229, shown in FIG. 3, is a pUC18-based expression vector containing a unique Bam HI site for insertion of cloned DNA between the mouse metallothionein-1 promoter and SV40 transcription terminator and an expression unit containing the SV40 early promoter, mouse dihydrofolate reductase gene and SV40 terminator. Zem229 was modified to delete its two Eco RI sites by partial digestion with Eco RI, blunting with DNA polymerase I (Klenow fragment) and dNTPs, and religation. Digestion of the resulting plasmid with Bam HI followed by ligation of the linearized plasmid with Bam HI-Eco RI adapters resulted in a unique Eco RI cloning site. The resultant plasmid was designated Zem229R. Zem229R was digested with Hind III and Eco RI, and the 520 bp fragment containing the SV40 and MT-1 promoters was removed. The large fragment of Zem229R was then joined to the ~1100 bp Hind III-Eco RI fragment of pDX (Hagen et al., U.S. Pat. No. 4,784,950), which contains the SV40 promoter/enhancer, the adenovirus major late promoter and a set of splicing signals. The resultant vector was designated ZMB4 (FIG. 3).

Plasmid ZMB4 containing a ca. 4 kb cDNA inserted at the Eco RI site (designated pM296-10) has been deposited with American Type Culture Collection, Rockville, Md. under Accession Number 67960. The vector may be regenerated from the deposited plasmid by digestion with Eco RI and re-ligation of the ca. 4.9 kb fragment.

The α-receptor sequences were removed from pα17B by digestion and were inserted into Bam HI-digested ZMB4. The resulting vector, designated α17/ZMB4, is transfected into cultured BHK 570 cells and receptor-producing clones are selected.

We claim:

1. An isolated DNA molecule encoding a human platelet-derived growth factor α-receptor, wherein said receptor comprises the amino acid sequence of FIG. 1 from leucine, amino acid number 20, to leucine, amino acid number 1089.

2. The DNA molecule of claim 1, wherein said molecule comprises the nucleotide sequence of FIG. 1 from nucleotide number 262 to nucleotide number 3471.

3. The DNA molecule of claim 1, wherein said molecule comprises the nucleotide sequence of FIG. 1 from nucleotide 205 to nucleotide 3471.

4. The DNA molecule of claim 1, wherein said molecule encodes the amino acid sequence of FIG. 1 from methionine, amino acid number 1, to leucine, amino acid number 1089.

5. Eukaryotic cells transfected or transformed with a DNA construct comprising a transcriptional promoter operably linked to a DNA molecule encoding a human platelet-derived growth factor α-receptor, wherein said receptor comprises the amino acid sequence of FIG. 1 from leucine, amino acid number 20, to leucine, amino acid number 1089.

6. The cells of claim 5, wherein said DNA molecule comprises the nucleotide sequence of FIG. 1 from nucleotide number 262 to nucleotide number 3471.

7. The cells of 5, wherein said DNA molecule comprises the nucleotide sequence of FIG. 1 from nucleotide 205 to nucleotide 3471.

8. The cells of claim 5, wherein said DNA molecule encodes the amino acid sequence of FIG. 1 from methionine, amino acid number 1, to leucine, amino acid number 1089.

9. The cells of claim 5, wherein said cells are cultured mammalian cells.

10. The cells of claim 5, wherein said cells are yeast cells.

* * * * *